United States Patent [19]

Snell

[11] Patent Number: 4,825,207

[45] Date of Patent: Apr. 25, 1989

[54] MONITORING OF FLUIDS

[75] Inventor: Julien D. Snell, Limpsfield, England

[73] Assignee: E.D.A. Research & Development Limited, London, England

[21] Appl. No.: 129,334

[22] Filed: Dec. 3, 1987

Related U.S. Application Data

[63] Continuation of Ser. No. 744,461, Sep. 10, 1985, abandoned.

[30] Foreign Application Priority Data

Sep. 15, 1984 [GB] United Kingdom ................ 8423369

[51] Int. Cl.[4] .............................................. H04Q 1/00
[52] U.S. Cl. ............................ 340/825.17; 340/825.06;
340/825.15; 324/61 R
[58] Field of Search ...................... 340/870.16, 870.17,
340/539, 825.06, 825.17, 825.15, 627, 565, 566;
73/53, 61.1 R, 61.1 C; 324/438, 61 R, 65 R;
137/5, 448

[56] References Cited

U.S. PATENT DOCUMENTS

| | | | |
|---|---|---|---|
| 2,675,540 | 4/1954 | Schultheis | 340/539 X |
| 3,573,817 | 4/1971 | Akers | 340/539 X |
| 3,636,544 | 1/1972 | Codina | 340/261 |
| 3,724,474 | 4/1973 | De Vale | 137/5 |
| 4,121,200 | 10/1978 | Colmenero | 340/539 |
| 4,154,660 | 5/1979 | Micko | 324/438 X |
| 4,187,502 | 2/1980 | Beverly et al. | 340/566 |
| 4,404,697 | 9/1983 | Hatcher | 4/492 |

Primary Examiner—Ulysses Weldon
Attorney, Agent, or Firm—Kinney & Lange

[57] ABSTRACT

An arrangement for monitoring conditions of a fluid comprising a first station incorporating a detector and transmitter assembly including a plurality of condition sensors, each of which is adapted to monitor one or more conditions of a fluid, receipt circuits adapted to receive signals from the sensors, a radio transmitter circuit fed from the receipt circuits; and a second station incorporating a receiver and output assembly including a radio decoding circuit for receiving signals from the transmitter circuit, incorporating a sub-circuit for separating and decoding signals from each of the conditions sensors, and a sub-circuit for converting these signals to a common voltage range, and an output circuit for translating the signal voltages to appropriate signal values for a visual and/or audio output.

11 Claims, 4 Drawing Sheets

MONITORING OF FLUIDS

This is a continuation of application Ser. No. 744,461, filed Sept. 10, 1985, now abandoned.

BACKGROUND OF THE INVENTION

This invention relates to apparatus for and methods of monitoring fluids. More particularly, although not exclusively, the invention is related to apparatus for and methods of monitoring a range of conditions of liquids such as water in a swimming pool, hot tubs, whirlpool or jacuzzi.

With such water utilising equipment it is frequently desirable to be able to monitor at regular intervals conditions such as temperature, clarity, chlorine level, and pH value of the water. This is particularly so for example in health clubs and similar organisations where such equipment can be subject to heavy use and operating codes of practice require a stringent monitoring timetable.

It is an object of the present invention to provide a convenient and effective arrangement for monitoring liquid conditions.

SUMMARY OF THE INVENTION

According to one aspect of the invention there is provided apparatus for monitoring conditions of a fluid comprising a first station incorporating a detector and transmitter assembly including a plurality of conditions sensors, each of which is adapted to monitor one or more conditions of a fluid, receipt circuits adapted to receive signals from the sensors, a radio transmitter circuit, fed from the receipt circuits; and a second station incorporating a receiver and output assembly including a radio decoding circuit for receiving signals from the transmitter circuit, incorporating a sub-circuit for separating and decoding signals from each of the condition sensors, and a sub-circuit for converting these signals to a common voltage range, and an output circuit for translating the signal voltages to appropriate signal values for a visual and/or audio output.

The first station receipt circuits may include amplifier and offset circuits.

According to another aspect of the invention there is provided a method of monitoring fluid conditions by obtaining signals from sensors detecting a plurality of conditions; amplifying such signals and transmitting them via a radio transmitter to a receiver; decoding and separating the signals with respect to the separate elements at the receiver and converting the same into signal voltages; and passing such signal voltages to a visual and/or audio output.

The second station may include a radio transmitter circuit adapted to receive signals from one or more control circuits and transmit command signals to the first station or elsewhere to operate fluid controlling mechanisms.

Such fluid controlling mechanisms may comprise a fluid pump or a heater for example.

Alternatively radio control of, for example, heaters and pumps for a swimming pool, may be provided by a radio control system separate from the second station.

The transmitter circuit in the first station may be arranged to transmit signals from each of the probe sensors at different frequencies, or in pulse width variations which are emitted form the transmitter and detected and separated by the receiver.

Appropriate circuits may be provided in the first station for converting the signal voltages from each of the sensors to a common voltage range. Similarly circuits may be provided for converting signals received by the receiver circuit in the second station to a common voltage range for feeding to the visual/audio output circuit.

The second station may incorporate an appropriate matrix selector such as a keyboard for operator usage for selecting from the plurality of separate signals received from the transmitter for forwarding on to the visual/audio output circuit. By this means it is possible for example, for the user to see in ordered sequence, readings on a visual display unit corresponding to the various conditions being monitored. The matrix selector may include keys for operating command signal transmissions.

Conveniently, the output may comprise an LED or LCD unit, and/or may include warning lights and/or warning audio outputs if received signals deviate beyond a predetermined required range.

In relation to a swimming pool, sensors may be provided for detecting the pH value of the water, the level of chlorination, the temperature in degrees Centigrade and/or degrees Fahrenheit, and the water clarity.

It is to be noted that the second station may comprise a visual display unit of semi-fixed nature which can be adapted to show one or more of the signals representative of the conditions of the liquid simultaneously, or can comprise a hand held unit adapted to show on a display, such as liquid crystal display, signals representative of each of the conditions to be monitored in turn by depression of an appropriate switch on the unit.

BRIEF DESCRIPTION OF THE DRAWINGS

In order that the invention may be more readily understood, a number of embodiments thereof will now be described by way of example with reference to the accompanying drawings in which.

DETAILED DESCRIPTION OF PREFERRED EMBODIMENTS

Figure 1:
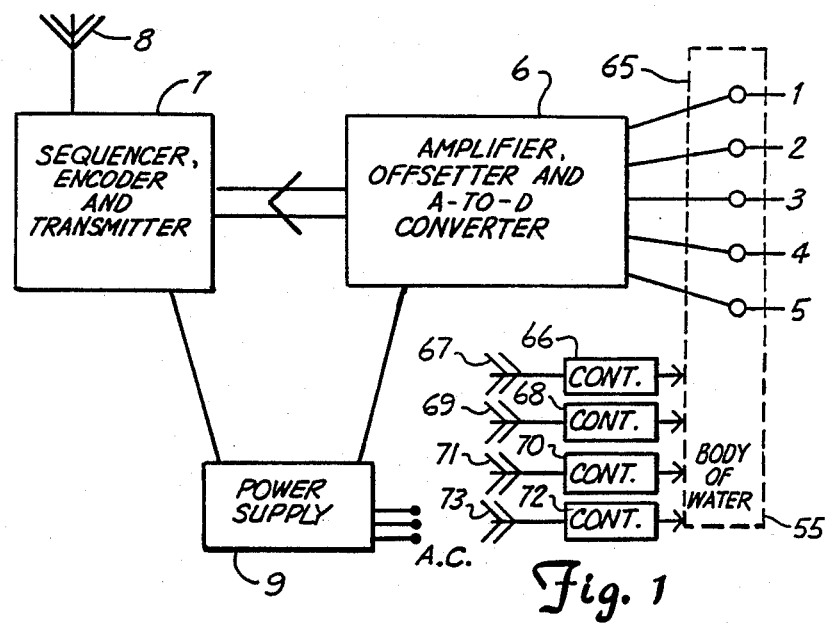
FIG. 1 is a block diagram of a first station of apparatus for monitoring various conditions of a swimming pool.
Figure 2:
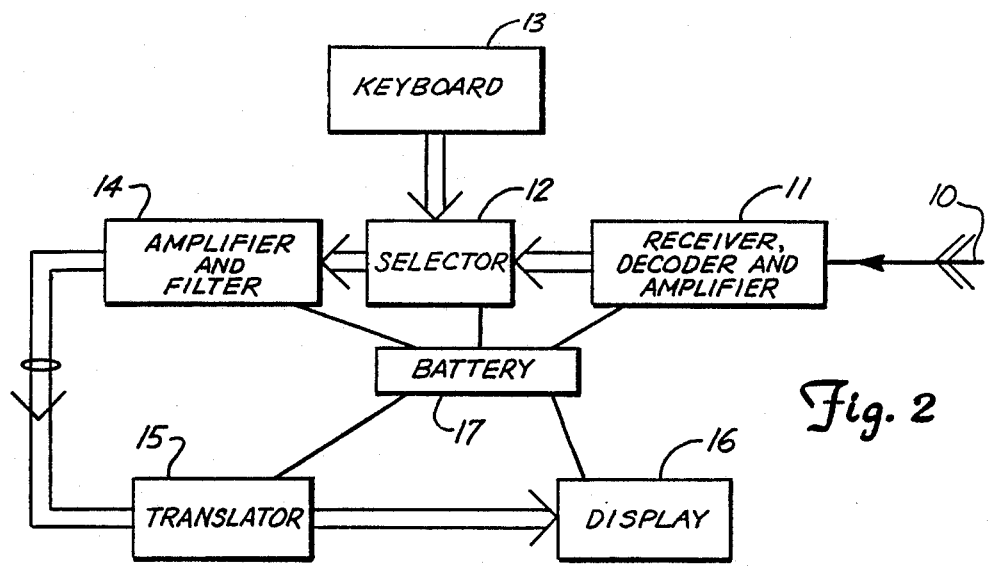
FIG. 2 is a block circuit diagram of a second station of apparatus for monitoring various conditions of a swimming pool.

Referring to the FIGS. 1 and 2 of the drawings it will be seen that the first station includes a plurality of sensors 1, 2, 3, 4 and 5 which are in practice located in a swimming pool 65 shown in dashed lines. Sensor 1 is a pH probe for detecting the pH value of the pool water, sensor 2 is a selective ion probe for detecting the chlorine level in the water, sensors 3 and 4 are thermocouples or thermistors for centigrade and fahrenheit temperature measurements, and sensor 5 is an infra-red detector of water clarity. All these detectors operate at somewhat different signal levels, but, typically, sensor 1 gives an output of 18 millivolts.

The analogue output signals from the sensors are fed to circuitry 6 including separate amplifying circuits and offset voltage applying circuits for each sensor, where the analogue input signals are converted to digital voltage signals and a voltage is superimposed upon the voltage signal such as to raise the overall voltages of each signal to the order of 500 microvolts. Each of the outputs is then fed to a transmitting circuit 7 where each of the signals are transmitted via aerial 8 sequentially in pulsed frequencies in encoded chains of pulses. Power supply for the circuits from 240 volts mains voltage is via a stabilised power rectified supply 9 at 12 volts. Typically, the transmitter has an output of 500 mW operating on 270 Khz A M or 35 Mhz F M.

At the second station the pulse train is received at aerial 10 and at circuit 11 is decoded into separate signal trains for each of the sensors and transmitted on as amplified signal voltages of varying magnitude between 0 and 500 mv. The signals then pass through a selection circuit 12 operated by a keyboard matrix 13 which enables just one set of signals representative of one sensor to pass through an amplifier and smoothing circuit 14 at which a further offset voltage is superimposed to bring the overall voltage within the magnitude of 0 to 2 volts. This voltage signal is then passed to a translation circuit 15 where the voltage is converted for display on a liquid crystal or gas plasma/L.E.D. display unit 16. Power for the receiver and output station is provided by a 9v battery 17.

Figure 3:
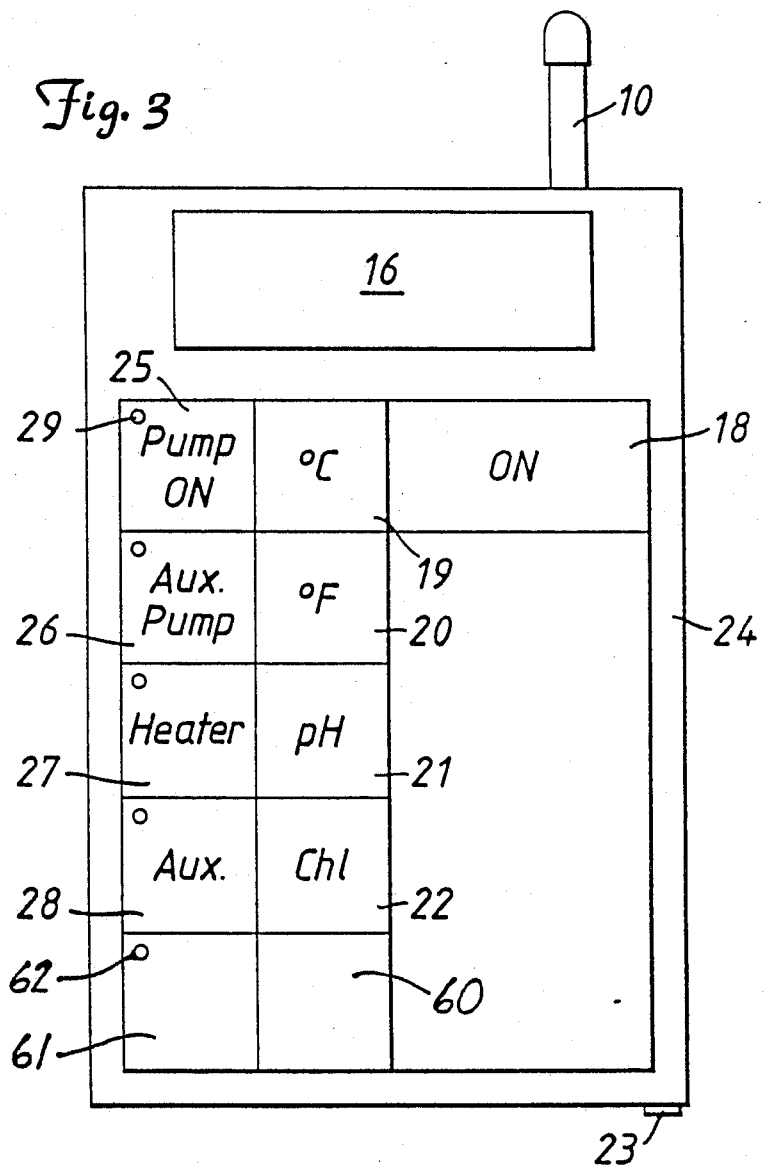
FIG. 3 illustrates a typical casing for a variant of the circuit of FIG. 2.

FIG. 3 illustrates a hand held case 24 for a variant of the second station illustrated in FIG. 2. The case 24 is provided with an on/off switch 18 and keys 19, 20, 21, 22 connected to a keyboard maxtrix for operation of a selection circuit. Display unit 16 is located at one end of the case 24 as is aerial 10. In this instance, control keys 25, 26, 27 and 28 are provided under a touch membrane for initiating the radio transmission of operating signals to a pool pump and associated receiver 66 with its aerial 67, auxiliary pump and associated receiver 68 with its aerial 69, heater and associated receiver 70 and its aerial 71, and auxiliary heater and associated receiver 72 with its aerial 73. Each of the keys 25, 26, 27 and 28 incorporates a status lamp 29, indicating the operating condition of the associated mechanism. The assembly may be powered by batteries rechargeable via port 23. Spare keys and lamp 60, 61, and 62 for any other required parameter are provided.

Figure 4:
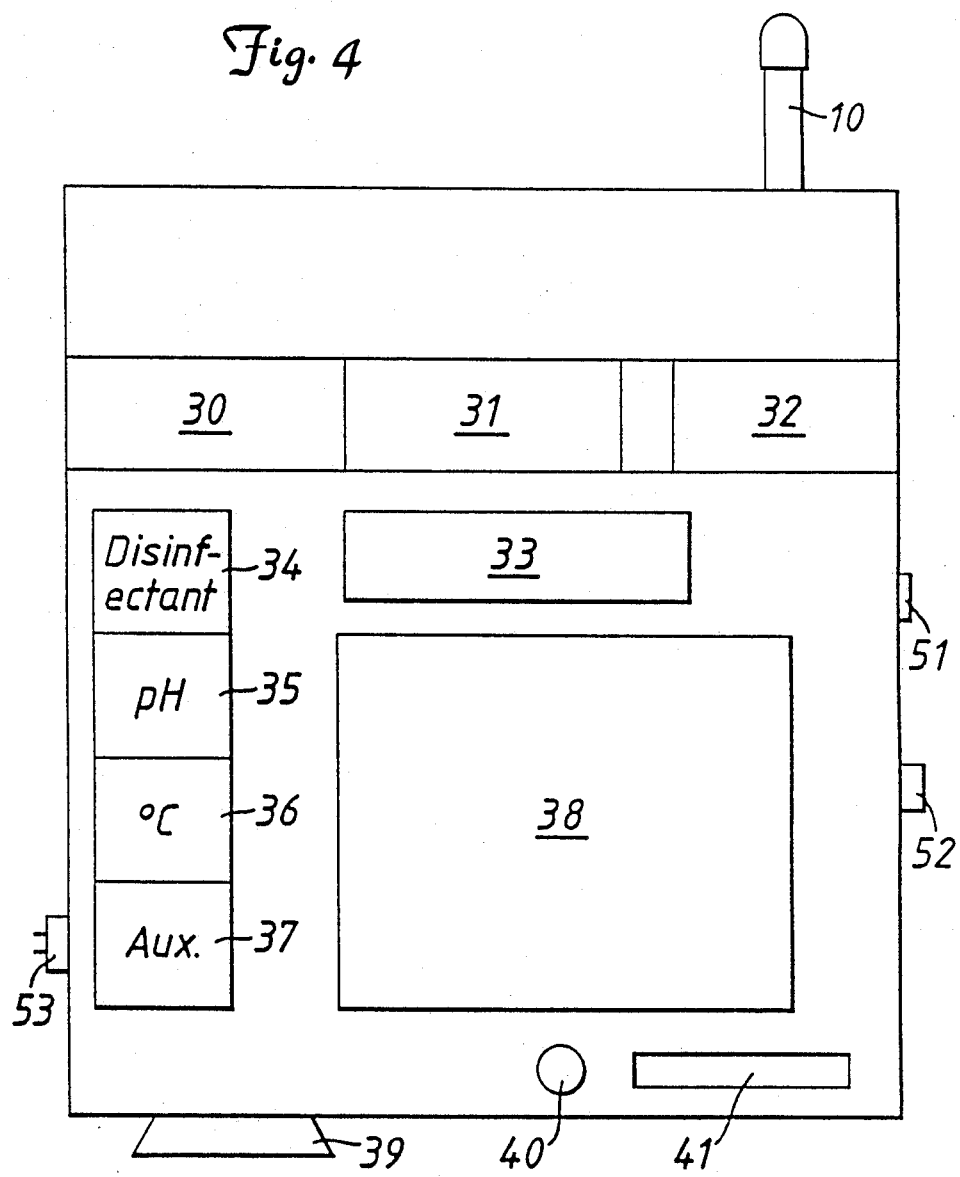
FIGS. 4 illustrates another casing for use with another embodiment of the invention.

FIG. 4 illustrates a somewhat more elaborate desk top assembly containing the second station. As can be seen this provides a plurality of LCD displays 30, 31 and 32 for display monitoring various swimming pool characteristics such as pH, disinfectant levels, and temperature in ° C. or in ° F. Other displays for water clarity pump flow rate, pump pressure rate and power consumption for example can be provided.

A keyboard 38 is included for programming a computer for control purposes, the computer being connectable via terminal 39, whilst a full computer display may be connected via socket 40.

Set points for disinfectant level, ph, ° C. for example may be established by keys 34, 35, 36 and 37 in conjunction with an alpha-numeric display 33 and the computer keyboard 38.

Sockets 51, 52 and 53 may be provided for probes, ancillary equipment, and for connection to chemical pumps for example.

The computer may have facility for future projection of pool conditions and states, and may be used for automatic chemical dosing. The case may incorporate an alarm.

In a typical arrangement, power will be from rechargeable batteries, and the device will have a radio transmission/reception range of 1 Km. The circuitry will include pulse coding for individual identification. Temperature range monitors may be between 10° C. and +100° C., and 20° F. to 240° F. pH 10 variations between 4.00 and 10.00 may be measured, for example.

Figure 5:
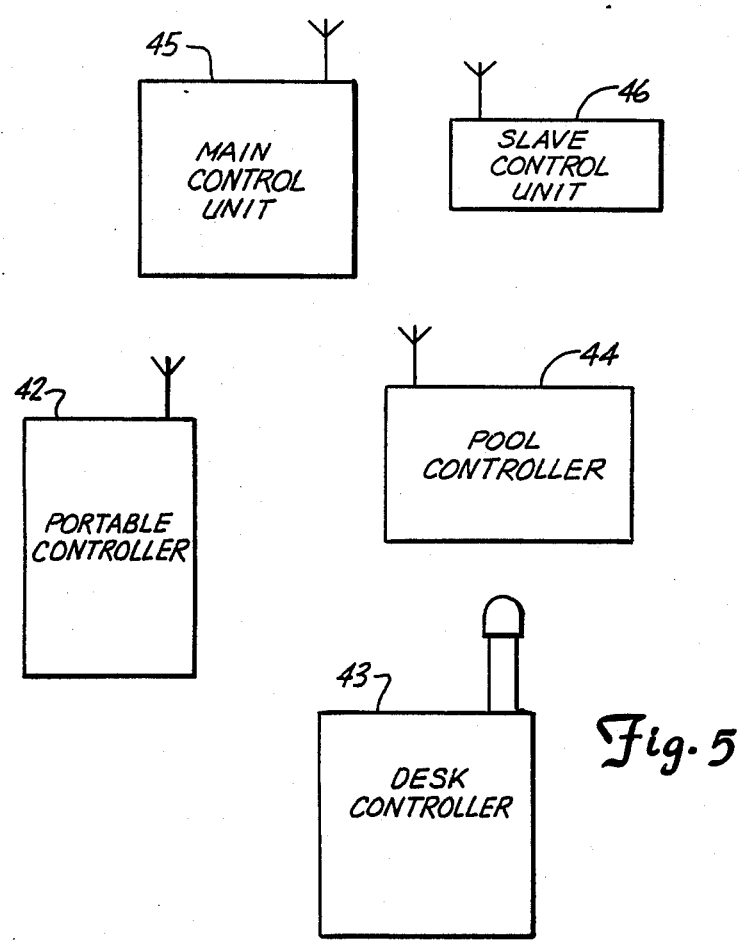
FIG. 5 illustrates diagrammatically a control system.

FIG. 5 shows possible control system for a swimming pool, in which there are provided three alternative controls units: a hand held controller 42; a Desk top controller 43; and a within pool controller 44. These are used for monitoring and signalling by radio transmission to a main control unit 45 located in a pool pump house for example, and at least one localised and specific slave power control unit 46.

By means of the invention we have provided a most convenient and practical arrangement for the monitoring of fluid conditions.

In addition to the embodiments above the invention can find most useful application as follows: ship sewage and bridge water systems; drinking water supplies; sewage water monitoring; monitoring emission gases such as in industrial chimneys and exhaust systems; fire monitoring, remote gas leak sensing; and fish farming water monitoring, for example.

I claim:

1. Apparatus for monitoring a first set of parameters of that water contained in a body of recreational water subject to having a second set of parameters directly controlled by water controlling mechanisms comprising a first station incorporating a plurality of sensors each of which is adapted to provide signals indicating values of at least one of said first set of parameters, receipt circuit means adapted to receive signals from the sensors, a first radio transmitter circuit fed from the receipt circuit means; a second station separable from the first station and the water controlling mechanisms, and incorporating a radio receiving circuit for receiving signals from the first radio transmitter circuit and separating signals form the first radio transmitter circuit due to each of the sensors, an output means providing visual and/or audio outputs based on the separated signals as received therein, control circuits selectively providing control signals based on the separated signals as received in the output means indicating the manner in which the water controlling mechanisms are to be operated, and a second radio transmitter circuit adapted to receive the control signals from one or more of the control circuits and transmit command signals based thereon; and at least one controller radio receiving circuit adapted for electrical connection to at least one of the water controlling mechanisms and for receiving the command signals, and further adapted to correspondingly operate that one of the water controlling mechanisms in controlling a corresponding one of said second set of parameters.

2. Apparatus as claimed in claim 1 wherein the first station receipt circuit means include amplifier and offset circuits.

3. Apparatus as claimed in claim 1 wherein the first radio transmitter circuit in the first station is arranged to transmit signals from each of the probe sensors at different frequencies which are detected and separated by the radio receiving circuit of the second station.

4. Apparatus as claimed in claim 1 wherein the first radio transmitter circuit in the first station is arranged to transmit signals from each of the probe sensors in pulse width variations which are detected and separated by the radio receiving circuit of the second station.

5. Apparatus as claimed in claim 1 wherein circuits are provided in the first station for converting the signals form each of the sensors to a voltage range common to each.

6. Apparatus as claimed in claim 1 wherein the second station incorporates an appropriate matrix selector for operator usage for selecting from the plurality of separate signals from the first radio transmitter circuit of the first station for forwarding on to the visual and-/or audio output circuit.

7. Apparatus as claimed in claim 1 wherein the output circuit includes a visual display unit and a warning signal output.

8. Apparatus as claimed in claim 1 for monitoring water conditions of a swimming pool serving as said body of recreational water wherein sensors are provided at least for detecting pH value of the water, level of disinfectant, temperature, and water clarity.

9. A method of monitoring conditions of a body of water by obtaining signals form sensors detecting a plurality of conditions; amplifying and encoding such signals and transmitting them via a radio transmitter to a remote receiver; decoding and separating the signals with respect to the separate sensors at the receiver and converting the same into signal voltages; passing such signal voltages to a visual and/or audio output; and transmitting by radio command, signals to operate remote water controlling mechanisms in dependence on the visual and/or audio output.

10. A method as claimed in claim 9 wherein the signals are transmitted at different frequencies which are detected and separated by the receiver.

11. A method as claimed in claim 9 wherein the signals are transmitted in pulse width variations which are detected and separated by the receiver.

* * * * *

UNITED STATES PATENT AND TRADEMARK OFFICE
CERTIFICATE OF CORRECTION

PATENT NO. : 4,825,207

DATED : April 25, 1989

INVENTOR(S) : Julien D. Snell

It is certified that error appears in the above-identified patent and that said Letters Patent is hereby corrected as shown below:

Col. 4, line 40, delete "form", insert --from--.

Col. 5, line 5, delete "form", insert --from--.

Col. 6, line 4, delete "form", insert --from--.

Signed and Sealed this

Eighth Day of August, 1989

*Attest:*

DONALD J. QUIGG

*Attesting Officer*  *Commissioner of Patents and Trademarks*